(12) United States Patent
Vogt et al.

(10) Patent No.: US 8,895,098 B2
(45) Date of Patent: Nov. 25, 2014

(54) COATING METHOD AND COATING DEVICE

(75) Inventors: Sebastian Vogt, Erfurt (DE); Hubert Büchner, Nuremberg (DE)

(73) Assignee: Heraeus Medical GmbH, Wehrheim (DE)

( * ) Notice: Subject to any disclaimer, the term of this patent is extended or adjusted under 35 U.S.C. 154(b) by 142 days.

(21) Appl. No.: 13/331,351

(22) Filed: Dec. 20, 2011

(65) Prior Publication Data

US 2012/0164311 A1 Jun. 28, 2012

Related U.S. Application Data

(60) Provisional application No. 61/432,782, filed on Jan. 14, 2011.

(30) Foreign Application Priority Data

Dec. 23, 2010 (DE) .......................... 10 2010 055 561

(51) Int. Cl.
| | | |
|---|---|---|
| *B05C 3/02* | (2006.01) | |
| *B05D 3/10* | (2006.01) | |
| *B05D 1/24* | (2006.01) | |
| *B05D 1/18* | (2006.01) | |
| *B05D 1/28* | (2006.01) | |
| *A61L 27/32* | (2006.01) | |
| *C23C 24/00* | (2006.01) | |
| *A61L 27/54* | (2006.01) | |

(52) U.S. Cl.
CPC .............. *C23C 24/00* (2013.01); *A61L 2430/24* (2013.01); *A61L 2420/02* (2013.01); *B05D 1/28* (2013.01); *A61L 27/32* (2013.01); *A61L 2300/406* (2013.01); *A61L 2420/06* (2013.01); *A61L 27/54* (2013.01)

USPC ....... 427/2.1; 427/2.24; 427/2.25; 427/430.1; 427/180; 118/400; 118/412

(58) Field of Classification Search
USPC .................... 427/430.1, 2.24, 2.1, 2.25, 180; 118/400

See application file for complete search history.

(56) References Cited

U.S. PATENT DOCUMENTS

| | | | |
|---|---|---|---|
| 4,532,929 A | * | 8/1985 | Mattei et al. ................ 606/230 |
| 4,846,837 A | | 7/1989 | Kurze et al. |
| 5,607,685 A | | 3/1997 | Cimbollek et al. |

(Continued)

FOREIGN PATENT DOCUMENTS

| | | |
|---|---|---|
| CN | 101406711 A | 4/2009 |
| CN | 101485901 A | 7/2009 |

(Continued)

OTHER PUBLICATIONS

Office Action issued Jul. 5, 2011 in DE Application No. 10 2010 055 561.4.

(Continued)

*Primary Examiner* — Cachet Sellman
(74) *Attorney, Agent, or Firm* — Panitch Schwarze Belisario & Nadel LLP

(57) ABSTRACT

A device for coating at least regions of a medical implant including a powder having at least one pharmaceutically active substance or one bone growth-promoting substance such that the powder can be transferred to the medical implant when the medical implant is contacted.

4 Claims, 2 Drawing Sheets

(56) References Cited

U.S. PATENT DOCUMENTS

| | | | |
|---|---|---|---|
| 5,614,206 A | 3/1997 | Randolph et al. | |
| 5,679,646 A | 10/1997 | Cimbollek et al. | |
| 5,756,127 A | 5/1998 | Grisoni et al. | |
| 5,759,376 A | 6/1998 | Teller et al. | |
| 5,807,567 A | 9/1998 | Randolph et al. | |
| 6,368,658 B1 * | 4/2002 | Schwarz et al. | 427/2.15 |
| 6,523,690 B1 | 2/2003 | Buck et al. | |
| 6,652,887 B1 | 11/2003 | Richelsoph et al. | |
| 6,743,463 B2 | 6/2004 | Weber et al. | |
| 6,764,769 B2 | 7/2004 | Kotte et al. | |
| 7,030,093 B2 | 4/2006 | Vogt et al. | |
| 7,563,324 B1 * | 7/2009 | Chen et al. | 118/270 |
| 2002/0110541 A1 | 8/2002 | Petersen | |
| 2002/0197315 A1 | 12/2002 | Haggard et al. | |
| 2005/0031664 A1 | 2/2005 | Vogt et al. | |
| 2006/0029722 A1 | 2/2006 | Larson et al. | |
| 2006/0134160 A1 | 6/2006 | Troczynski et al. | |
| 2006/0188541 A1 | 8/2006 | Richelsoph et al. | |
| 2006/0251824 A1 | 11/2006 | Boulais et al. | |
| 2007/0125247 A1 | 6/2007 | Kunstmann et al. | |
| 2007/0281072 A1 | 12/2007 | O'Connor et al. | |
| 2008/0206442 A1 | 8/2008 | Shekalim et al. | |
| 2010/0185299 A1 | 7/2010 | Nies | |
| 2010/0286790 A1 | 11/2010 | Gruner et al. | |
| 2011/0287064 A1 | 11/2011 | Vogt et al. | |

FOREIGN PATENT DOCUMENTS

| | | | |
|---|---|---|---|
| DE | 4404018 A1 | 8/1995 | |
| DE | 4431862 A1 | 3/1996 | |
| DE | 10142465 A1 | 7/2003 | |
| DE | 10351150 A1 | 5/2005 | |
| DE | 60309460 T2 | 9/2007 | |
| EP | 0232791 A2 | 8/1987 | |
| EP | 0306212 A2 | 3/1989 | |
| EP | 306212 A2 * | 3/1989 | |
| EP | 0623349 A1 | 11/1994 | |
| EP | 1264606 A1 | 12/2002 | |
| EP | 1374923 A2 | 1/2004 | |
| EP | 1470829 A1 | 10/2004 | |
| EP | 2392360 A2 | 12/2011 | |
| WO | 2004024201 A2 | 3/2004 | |
| WO | 2004098436 A2 | 11/2004 | |
| WO | 2005037447 A1 | 4/2005 | |
| WO | 2005042045 A1 | 5/2005 | |
| WO | 2007147246 A1 | 12/2007 | |
| WO | 2008064672 A2 | 6/2008 | |
| WO | 2009062671 A2 | 5/2009 | |
| WO | 2009147045 A1 | 12/2009 | |
| ZA | 200206983 A | 5/2003 | |

OTHER PUBLICATIONS

Search Report issued May 11, 2012 in EP Application No. 11009583.3.

De Groot et al, "Calcium phosphate coatings for medical implants," Proceedings of the Institution of Mechanical Engineers, vol. 212, Part H, pp. 137-147 (1998).

Notice of Acceptance issued May 31, 2013 in AU Application No. 2011253929.

Office Action issued May 13, 2013 in CA Application No. 2,760,900.

Office Action issued May 8, 2014 in DE Application No. 10 2010 055 561.4.

* cited by examiner

COATING METHOD AND COATING DEVICE

CROSS-REFERENCE TO RELATED APPLICATIONS

The present application claims priority to U.S. Provisional Patent Application No. 61/432,782, entitled "Coating Process and Coating Apparatus" and filed Jan. 14, 2011.

BACKGROUND OF THE INVENTION

The present invention relates generally to a method for coating, at least regions of, a medical implant, preferably of an artificial joint or a fixation for a joint.

The present invention also relates generally to a device for coating, at least regions of, a medical implant using the method.

The coating of medical implants with pharmaceutical agents has garnered increasing attention in recent years. Antibiotic protection of the surface of implant materials is a central application of coating methods in this context. The improvement of the surface compatibility of non-cemented medical implants in order to improve osseointegration is another important application.

Any implantation of articular endoprostheses, and of osteosynthesis materials as well, is associated with a certain risk of microbial contamination. Successful colonization of microbial pathogens on the surface of the implant can lead to the manifestation of post-operative osteitis/osteomyelitis. Osteitis/osteomyelitis is a severe complication for the patient and, in addition, is associated with substantial costs.

Gentamicin-doped PMMA bone cement has been in clinical use with cemented articular endoprostheses for decades with much success. The broadband antibiotic, gentamicin, contained in the bone cement protects the surface of the bone cement effectively from bacterial infections.

With regard to non-cemented articular endoprostheses and osteosynthesis materials, a number of approaches has been proposed in order to also attain local antibiotic protection of the implant surfaces.

For example, the use of poorly water-soluble antibiotic salts has been described in several patent documents. For exemplary purposes, EP 0 623 349 A1, EP 1 470 829 A1, EP 1 374 923 A2, DE 101 42 465 A1, and DE 44 04 018 A1 can be cited in this context. The poorly water-soluble salts dissolve while releasing the antibiotics contained therein as a result of the action of body fluids. Prolonged release of the agent is advantageous. However, the laborious production of the salts is disadvantageous.

Alternatively, it is feasible to use water-soluble antibiotic salts. This is associated with a problem related to fixation of the antibiotic on the implant surface.

The majority of coatings that have been described thus far is preferably intended for the manufacture of coated implants under industrial conditions. This means that the industrial coating of the implants can only involve few agents that are relevant for large-scale use in order to be able to guarantee that the industrial manufacture is economic through sufficiently large throughput.

In particular in the case of antibiotic coatings, though, considering the increasingly problematic resistance status and the ensuing increased manifestation of multi-resistant pathogens, such as MRSA and MRSE, it is of interest to use antibiotics or combinations of antibiotics, which are specifically adapted to the germ at hand, for the coating of revision prostheses in one-stage or two-stage septic articular endoprosthesis replacement in order to ensure effective initial antibiotic protection of the implant surfaces.

This is disadvantageous in that the methods for coating the medical implants are relatively laborious. Variable short-term application is not feasible. Various scenarios then necessitate the stock-keeping of various coated medical implants in order to meet the needs of the different patients. This requires extensive stock-keeping and prevents uncommon mixtures for specific cases.

In general, non-cemented articular endoprostheses are made from titanium alloys and usually have a surface that is roughened (for example through sand-blasting) or structured and porous in order to improve the integration of bone tissue. The alloys used thus provide for assured mechanical stability and integrity. For this reason, it was attempted to improve the compatibility of the implant surfaces with respect to the bone tissue. The mineral phase of human bone tissue is provided by a carbonate apatite/hydroxyl apatite. Therefore, the main emphasis of improving the compatibility of surfaces of medical implants is on the development of calcium phosphate layers.

A broad range of methods (thermal injection procedures, electrochemical deposition, sol-gel technologies, ion beam sputtering, laser ablation) have been used in attempts to attain an improvement of the surface compatibility at the contact site with the bone tissue (hip, knee, shoulder joint endoprostheses). Thus far, on an industrial scale, only the plasma spraying procedure (De Groot et al.: Plasma-sprayed coatings of calcium phosphate. CRC Press, Boca Raton, Ann Arbor, Boston, 1990; De Groot et al.: Chemistry of calcium phosphate bioceramics. CRC Handbook of bioactive ceramics, 2, 1996, 3-16; WO 2009/062671 A2) and electrochemical deposition of calcium phosphate layers (Ban and Maruno: Morphology and microstructure of electrochemically deposited calcium phosphates in a modified simulated body fluid. Biomaterials, 19, 1998, 1245-1253; DE 44 31 862 A1; WO 2009/147045 A1; CN 101485901 A; CN 101406711 A; WO 2007/147246 A1; US 2006/134160 A1; WO 2004/098436 A2; WO 2004/024201 A2; EP 1 264 606 A1; EP 0 232 791 A2) have become established. Printed publications US 2002/110541 A1, U.S. Pat. No. 5,807,567 A, US 2002/197315 A1, U.S. Pat. No. 6,652,887 B1, U.S. Pat. No. 5,756,127 A, and U.S. Pat. No. 5,614,206 A describe bone replacement materials which essentially consist of a mixture of $\alpha$- and $\beta$-calcium phosphate and are designed for use as "drug delivery" systems for pharmaceutical agents.

However, clinical long-term studies have shown that plasma-sprayed calcium phosphate layers, although generally considered to be stable in the long term, are subject to partial degradation in their biological environment. There are not only phase changes at the boundary to the bone tissue, but also the process leads to encapsulation and/or flaking off, predominantly of crystalline components of the layer, and thus to interfering particles.

It is another disadvantage that all electrochemical deposition methods that are common thus far necessitate a substantial equipment and time effort in order to be able to apply the calcium phosphate layers to the articular endoprosthesis.

BRIEF SUMMARY OF THE INVENTION

Accordingly, it is a objective of a preferred embodiment of the present invention to overcome the disadvantages of the prior art. In particular, a simple and easy-to-use method and a device are to be provided for this purpose that can be used to coat a medical prosthesis without interfering with an ongoing surgery (OR). The aim is to be able to coat as many different medical implants as possible using the same method and the same device. Moreover, the method and the device should be variable to use such that they can be adapted to the medical needs, in particular to a suitable medication for the patient. The cleanliness required in operating theatres is another factor to take into account.

It is also an objective of a preferred embodiment of the present invention to develop a coating method that is as simple as possible and can be used by the OR staff during an ongoing surgery, with the least time expenditure, to coat very different implants from any manufacturers with pharmaceutical preparations. Moreover, it is an objective of a preferred embodiment of the present invention to develop a simple coating device that allows the OR staff to coat implants under OR conditions with the least effort possible. Moreover, the device is to be designed such that, to the extent possible, no excess material from the production of the coating can contaminate the OR area. Another objective is that the device should, in particular, be suitable for the coating of non-cemented articular endoprostheses and osteosynthesis materials.

The objective of a preferred embodiment of the present invention is met in that a medical implant having a surface to be coated is provided and the medical implant surface to be coated is contacted with a powder that comprises at least one pharmaceutically active substance and/or one bone growth-promoting substance, whereby powder is transferred to the surface of the medical implant through the contacting, and at least part of the powder adheres to the surface to be coated after the contacting. Preferably, the contacting proceeds such that the medical implant surface to be coated is immersed into a powder comprising at least one pharmaceutically active substance and/or one bone growth-promoting substance or is pressed onto the powder, whereby the immersing or pressing causes powder to be transferred to the surface of the medical implant, and the surface to be coated is then pulled out of the powder or the pressure is released, whereby at least part of the powder adheres to the surface to be coated.

Methods according to a preferred embodiment of the present invention are carried out before inserting the medical implants. Accordingly, the methods proceed "ex vivo."

According to a preferred embodiment of the present invention, a pharmaceutically active substance shall be understood to mean pharmaceutically effective means or means with a pharmacological effect as well as means that support a pharmacological effect or support in any other way the self-healing forces of the body. Examples include antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof.

According to a preferred embodiment, the contacting with the powder proceeds through immersing into the powder or pressing onto the powder. According to a preferred embodiment of the present invention, immersing is to be understood to not only mean immersing in a large quantity of the powder. The term, pressing-on, in the scope of the present invention, means, for example, that the powder is arranged at a surface that is shaped much like the medical implant to be coated such that just a thin layer of the powder is provided. Pressing-on the medical implant then leads to near complete transfer of the powder to the surface of the medical implant.

The scope of a preferred embodiment of the present invention also includes that the implant to be coated is introduced into and pulled out of the device repeatedly, if applicable.

Moreover, a preferred embodiment of the present invention can provide the medical implant to be coated to be selected from non-cemented hip endoprostheses, shoulder joint endoprostheses, elbow endoprostheses, marrow nails, and osteosynthesis plates.

According to a particularly advantageous refinement, a preferred embodiment of the present invention can provide the medical implant surface to be coated to be contacted with a liquid, preferably to be immersed into a liquid or painted or wetted with a liquid, prior to contacting it with the powder, preferably prior to immersing it into the powder or pressing it onto the powder. The powder may adhere better to a liquid-wetted medical implant than to a dry medical implant. Moreover, the liquid also can comprise a pharmaceutically active substance.

In this context, the scope of a preferred embodiment of the present invention can also provide that the liquid comprises an aqueous solution of an antibiotic, preferably that an aqueous gentamicin sulfate solution with a gentamicin sulfate content of 10.0 to 88.0% by weight is used, whereby it is particularly preferred to use a gentamicin sulfate solution with a gentamicin sulfate content of 75.0 to 80.0% by weight. The gentamicin sulfate solution has an oily-viscous consistency and adheres very well to metal surfaces.

In this context, a preferred embodiment of the present invention can further provide that common pharmaceutical stabilizers are contained in the gentamicin sulfate solutions. These improve the durability and thus the usability of the liquid to be applied.

A preferred embodiment of the present invention can also provide for the use of other aminoglycoside antibiotic solutions such as aqueous solutions of tobramicin sulfate, amikacin sulfate, netilmicin sulfate, and sisomicin sulfate as liquid or components of the liquid. It is also feasible to use aqueous solutions of vancomycin, dalbavancin, ramoplanin, daptomycin, moxifloxacin, clindamycin, and lincomycin.

Moreover, the scope of a preferred embodiment of the present invention can provide for the use of combinations of solutions of different antibiotics as liquid. Examples include two-antibiotic combinations of gentamicin sulfate and vancomycin hydrochloride, the two-antibiotic combination of daptomycin and gentamicin sulfate, and the two-antibiotic combination of gentamicin sulfate and clindamycin as well as the three-antibiotic combination of gentamicin sulfate and vancomycin hydrochloride and clindamycin hydrochloride.

A preferred embodiment of the present invention can further provide for antiseptics solutions to be used as liquid, in particular solutions of chlorohexidine digluconate, octenidine dihydrochloride, and polyhexanide.

In this context, methods according to a preferred embodiment of the present invention can be characterized in that the medical implant is being swept over a transfer means that can be deformed elastically, whereby a liquid, preferably comprising at least one pharmaceutically active substance, is transferred from the transfer means to the medical implant surface to be coated while sweeping over the transfer means. What using a transfer means that can be deformed elastically achieves is that the liquid applied by the transfer means can also be applied onto an irregularly shaped medical implant in a widespread manner. It is particularly preferred for the transfer means to also be porous, whereby the liquid is stored in the pores of the transfer means. The transfer means can then be arranged above the powder without the liquid dripping into the powder. This is advantageous, in particular in combination with a membrane for covering the powder.

Another refinement of the method according to a preferred embodiment of the present invention can provide the powder to be provided in a container having an opening, whereby the medical implant is introduced through the opening in order to coat the surface to be coated.

In this context, a preferred embodiment of the present invention can provide the medical implant to be introduced into the container, in which the powder is situated, before contacting it with the powder, preferably before immersing it into the powder or pressing it onto the powder, and to be pulled out of the container after transfer of the powder to the medical implant. Owing to the two measures, the method is easy to use at different sites, since the device to be used is easy to transport.

A preferred embodiment of the present invention can also provide that the medical implant is pushed through a membrane or a membrane is opened before contacting the medical implant with the powder, whereby the membrane covers at least regions of the powder, preferably the membrane covers all of the powder in the container. The membrane prevents the powder from being contaminated prior to its use. Puncturing the membrane ensures that the protective membrane is opened only shortly before its use. For this purpose, the structure of the membrane should be such that no shreds or other parts of the membrane can enter into the powder or adhere to the medical implant.

Another refinement of the method according to a preferred embodiment of the present invention can be to provide a powder that matches the treatment scenario.

A preferred embodiment of the present invention can also provide that an antibiotic or mixture of antibiotics matching the treatment scenario is introduced into the powder. These two measures allow for individual adaptation to the actual treatment scenario of the respective patient.

It is particularly preferred for the present invention to provide that part of the transferred powder is being wiped off, in particular upon pulling the medical implant out of the container, preferably at a wiper designed for this purpose. This can prevent or at least reduce contamination of the surroundings, for example, in particular of an OR area, by the powder and, if applicable, by the liquid. This is advisable especially upon the use of antibiotics since it allows the development of resistant pathogens in the OR area to be prevented.

Moreover, a preferred embodiment of the present invention can provide that at least 50% of the surface of the medical implant, preferably at least 80%, particularly preferably at least 90% of the surface of the medical implant, are being coated.

In order to render the coated region and the completeness of coating visible, the invention can provide that the powder is made to be colored such that the coated region of the medical implant can be identified by color.

In this context, a preferred embodiment of the present invention can provide that the completeness of coating of the region to be coated is tested by means of the coloration.

A preferred embodiment of the present invention can also provide for the method to be repeated as often as required for complete coating of the medical implant surface to be coated to be attained. In particular in the context of coloration of the liquid and testing of the completeness of coating through the coloration, this is advantageous according to the invention in order to generate a sufficiently coated medical implant.

Another refinement of a preferred embodiment of the present invention provides the powder to be whirled up through a flow of air in order to attain complete coating of the medical implant. It can be advantageous in this context for the container with the implant inserted into it to be closed and/or sealed at an earlier time. This can be done through closing a lid that is designed for this purpose.

Moreover, a preferred embodiment of the present invention can provide for brief shaking of the container with the implant.

The objective of a preferred embodiment of the present invention is also met by a device for coating, at least regions of, a medical implant using the method, whereby the device contains a powder, whereby the powder comprises at least one pharmaceutically active substance and/or one bone growth-promoting substance such that the powder can be transferred to the medical implant when a medical implant is contacted, preferably when a medical implant is immersed or pressed-on.

In this context, a preferred embodiment of the present invention can provide the powder to be arranged in a container comprising an opening for introducing and taking out the medical implant.

Moreover, a preferred embodiment of the present invention can provide the opening to be closed through a pull-off lid. This allows contamination of the inside of the container to be prevented.

A particularly advantageous refinement of a preferred embodiment of the present invention can provide the device to comprise a wiper that is preferably arranged in the region of the opening, in particular between the opening and the powder.

In this context, a preferred embodiment of the present invention can provide the wiper to be disc-shaped and to comprise at least one notch that connects the top and the bottom of the disc. The implant can be introduced into the device through the at least one notch. It is particularly advantageous to have radial notches formed in the wiper. This enables the entire external circumference of the implants to be wiped off after coating is complete and thus to remove excess quantities of the solution or suspension from the coated implant surface. Moreover, it enables to effectively counteract the release of droplets or particles of the powder and/or liquid that might arise upon pulling the implant out of the transfer means. Contamination during the surgery is thus largely prevented.

Moreover, a preferred embodiment of the present invention can provide the wiper to be shaped like an envelope of cone or a hemispherical surface, whereby the tip of the cone or the hemisphere is oriented towards the powder and the cone or the hemisphere preferably contain at least one notch that connects the top and the bottom of the wiper.

A preferred embodiment of the present invention can also provide a transfer means to be arranged above the powder that can be used to transfer a liquid to the medical implant, whereby the liquid is contained in the transfer means.

In this context, a preferred embodiment of the present invention can provide the transfer means to comprise pores and the pores of the transfer means to contain the liquid, preferably in the form of a solution and/or suspension, whereby the liquid preferably contains a second pharmaceutically active substance.

A refinement of a preferred embodiment of the present invention provides the transfer means to comprise at least one roller, at least one rotatable sphere and/or at least one sponge that can be used to transfer the liquid to the medical implant surface to be coated. This allows the quantity of the liquid to be used to be reduced and inadvertent mixing of major quantities of the liquid with the powder to be prevented.

According to a particularly preferred refinement, a preferred embodiment of the present invention can provide the powder, and preferably the liquid also, to contain antibiotics and/or organic antiseptic agents in a manner such that the coating to be generated contains a pharmaceutically active dose.

Moreover, a preferred embodiment of the present invention can provide the device to comprise a vacuum connection that can be connected to a vacuum source and is preferably arranged between the wiper and the powder. This can ensure, in addition, through the aspiration of any remnants of powder and droplets of the liquid, if applicable, that no contamination of the operating theatre through pharmaceutical agents occurs.

According to a preferred embodiment of the present invention, devices according to the present invention having a transfer means for the application of a liquid can provide the container and/or wiper to be manufactured preferably from a hydrophobic material and the transfer means to be manufactured preferably from a hydrophilic material. It is preferable to use aqueous solutions and/or suspensions of pharmaceutical agents for the liquid. Provided the transfer means is manufactured from a hydrophilic material, aqueous solutions and/or suspensions are preferably situated in the porous hydrophilic material, rather than on the hydrophobic surface of the container and of the wiper. This behavior allows coating devices pre-filled with aqueous solutions and/or suspensions to get by with even the least volumes of the aqueous solutions or suspensions and still allow for assured coating.

A preferred embodiment of the present invention can also provide for the wiper to be made of a biocompatible elastomer, thermoplastic material and/or a metal foil or composites that are manufactured from metal-elastomer combinations or metal-plastic combinations.

Moreover, a preferred embodiment of the present invention can provide the wiper as a ring that contains bristles that are arranged such as to be radial with respect to the centre of the container. The bristles can be made of plastic material, whereby the mechanical stability and anchoring of the bristles are sufficiently strong for the bristles to neither break off nor become detached, if at all possible.

According to a refinement, a preferred embodiment of the present invention provides the wiper in the form of rotatable or non-rotatable rollers and/or spheres that are connected to the container through elastic connecting means. The structure allows excess powder, and excess liquid, if applicable, to be wiped off particularly easily.

According to a preferred embodiment of the present invention, the device can be pre-filled with a powder, a solution and/or a suspension of an agent such that the OR staff simply needs to open the device and can then proceed with the coating of the implant instantaneously. In this context, it is advantageous that the time expenditure for the coating is in the range of but a few seconds and valuable OR time can thus be saved.

Alternatively, it is feasible to provide a non-pre-filled device with one or more pharmaceutical agents right in the OR through filling it with a powder and/or injecting a solution or suspension of an agent. In the case of the antibiotic coating, this enables suitable selection of an antibiotic or combination of antibiotics based on the existing resistance status and thus ensures that the coating matches the antibiotic sensitivity pattern.

It is also feasible to fill non-pre-filled devices with suitable solutions or suspensions of agents in the respective hospital pharmacy prior to surgery such that coating can be carried out during the surgery without any time delay.

Examples of pharmaceutically active substances that can be used include antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof.

According to a preferred embodiment of the present invention, aqueous solutions of an antibiotic, preferably an aqueous gentamicin sulfate solution with a gentamicin sulfate content of 10.0 to 88.0% by weight can be provided as liquids, whereby a gentamicin sulfate solution with a gentamicin sulfate content of 75.0 to 80.0% by weight is particularly preferred. The gentamicin sulfate solution has an oily-viscous consistency and adheres very well to metal surfaces. Moreover, common pharmaceutical stabilizers may also be present in the gentamicin sulfate solutions.

The scope of a preferred embodiment of the present invention also includes the use of other aminoglycoside antibiotic solutions such as aqueous solutions of tobramycin sulfate, amikacin sulfate, netilmicin sulfate, and sisomycin sulfate. It is also feasible to use aqueous solutions of vancomycin, dalbavancin, ramoplanin, daptomycin, moxifloxacin, clindamycin, and/or lincomycin. The use of combinations of solutions of various antibiotics is also included in the scope of the invention. Examples include two-antibiotic combinations of gentamicin sulfate and vancomycin hydrochloride, the two-antibiotic combination of daptomycin and gentamicin sulfate, and the two-antibiotic combination of gentamicin sulfate and clindamycin as well as the three-antibiotic combination of gentamicin sulfate and vancomycin hydrochloride and clindamycin hydrochloride. Moreover, it is feasible to use antiseptic agent solutions in place of antibiotic solutions. Examples include solutions of chlorohexidine gluconate, octenidine dihydrochloride or polyhexanide.

The scope of a preferred embodiment of the present invention also includes the use of solutions of antibiotics and antiseptic agents that contain, as solvents, organic solvents or combinations of organic solvents or combinations of organic solvents and water.

This allows, for example, poorly water-soluble antibiotic salts, such as laurates, myristates, palmitates, and stearates, to be used as well. Moreover, poorly water-soluble antibiotics or antibiotic salts in the form of aqueous suspensions can also be used.

According to a preferred embodiment of the present invention, the powder as bone growth-promoting substance comprises at least one compound selected from the group consisting of β-tricalcium phosphate, α-tricalcium phosphate, amorphous calcium phosphate, tetracalcium phosphate, octacalcium phosphate, hydroxylapatite, fluoroapatite, calcium sulfate hemihydrate, calcium sulfate dihydrate, anhydrous calcium sulfate, powdered antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof. The powder can also contain complexing agents or salts that form poorly water-soluble complexes or salts with the pharmaceutical agents that are transferred from the wiper to the implant surface. The powder can thus contain, for example, teicoplanin that forms poorly water-soluble complexes with gentamicin or other cationic antibiotics. It is also feasible, for example, that the powder contains N-methylglucammonium salts of fatty acids or of alkyl sulfates, which can form poorly water-soluble fatty acid salts or alkyl sulfates of the antibiotics upon exposure to aqueous solutions of cationic antibiotics owing to a reciprocal salt exchange. This means enables the application of poorly water-soluble complexes or salts of pharmaceutical agents, in particular of antibiotics, onto the implant surface.

It is particularly advantageous to use reactive inorganic powders, such as calcium phosphate made amorphous, tetracalcium phosphate and calcium sulfate hemihydrate, which harden in the presence of water. It is thus feasible to form stable coatings. Hardening within just a few seconds can be achieved, for example when calcium sulfate hemihydrate is used as the powder, through the addition of small amounts of calcium sulfate dihydrate as a nucleation agent and ammonium sulfate, sodium sulfate or potassium sulfate as accelerator to the calcium sulfate hemihydrate. Moreover, the use of β-tricalcium phosphate, α-tricalcium phosphate, and tetracalcium phosphate, which harden within just a few seconds upon exposure to the influence of aqueous acids, in particular of aqueous solutions of malic acid, tartaric acid, and citric acid, is also advantageous.

The scope of a preferred embodiment of the present invention further includes the provision of the device as a drug or medical product.

A combination of the device according to a preferred embodiment of the present invention and a medical implant could be offered as well. The combination is formed by the device and the implant, whereby the combination has a minimal service life of 0.1 seconds. The combination arises during the coating process.

A preferred embodiment of the present invention is based on the surprising finding that a powder to be used for coating a medical implant can be applied to a medical implant even shortly before its use through simply immersing the implant into the powder. The simple method and the device therefore ensure the usability in the OR area as well.

Studies demonstrate the high efficiency of fully degradable bioactive layers that were applied to metallic base bodies through electrochemical methods. The analysis of animal experiments and clinical studies leads to the conclusion that despite rapid and complete degradation of highly soluble calcium phosphate layers, assured osseointegration behavior at the implant surface is evident.

The rapidly soluble calcium phosphate layers can therefore lead to good clinical results. Therefore, no coating featuring long-term stability on the implant surfaces is required.

For initial antibiotic protection, it is sufficient to have sufficiently high concentration(s) of antibiotic or antibiotics at the implant surfaces for a period of 24 to 72 hours. Therefore, sufficient temporary local antibiotic protection of the medical implant can be attained even upon local introduction of simple water-soluble antibiotics into a liquid.

A fine powder adheres to a small extent even to purely metallic implants as a result of electronic interactions. The dust layer remaining on the medical implant after immersing it into the powder may already be sufficient to attain an improvement of the growth of bone substance in the region of the inserted medical implant. A thicker layer of powder can be generated through first coating the medical implant with a liquid. Advantageously, the liquid used for coating is also well-suited for application of an antibiotic contained in the liquid or of other water-soluble pharmaceutically effective substances to the medical implant. The coating thus generated can contain a large number of different substances. Since the substances are applied only shortly before insertion of the implant, even substances that are not easily miscible with the powder or liquid for an extended period of time, since they interfere with each other over time, can be admixed to the powder and liquid.

Accordingly, rather than coating the medical implant much earlier during its manufacture, it can also be coated right before inserting it. This allows relatively short-acting coatings to be used as well.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

Exemplary embodiments of the present invention shall be illustrated in the following on the basis of two schematic figures, though without limiting the scope of the invention. In the figures.

DETAILED DESCRIPTION OF THE INVENTION

Figure 1:
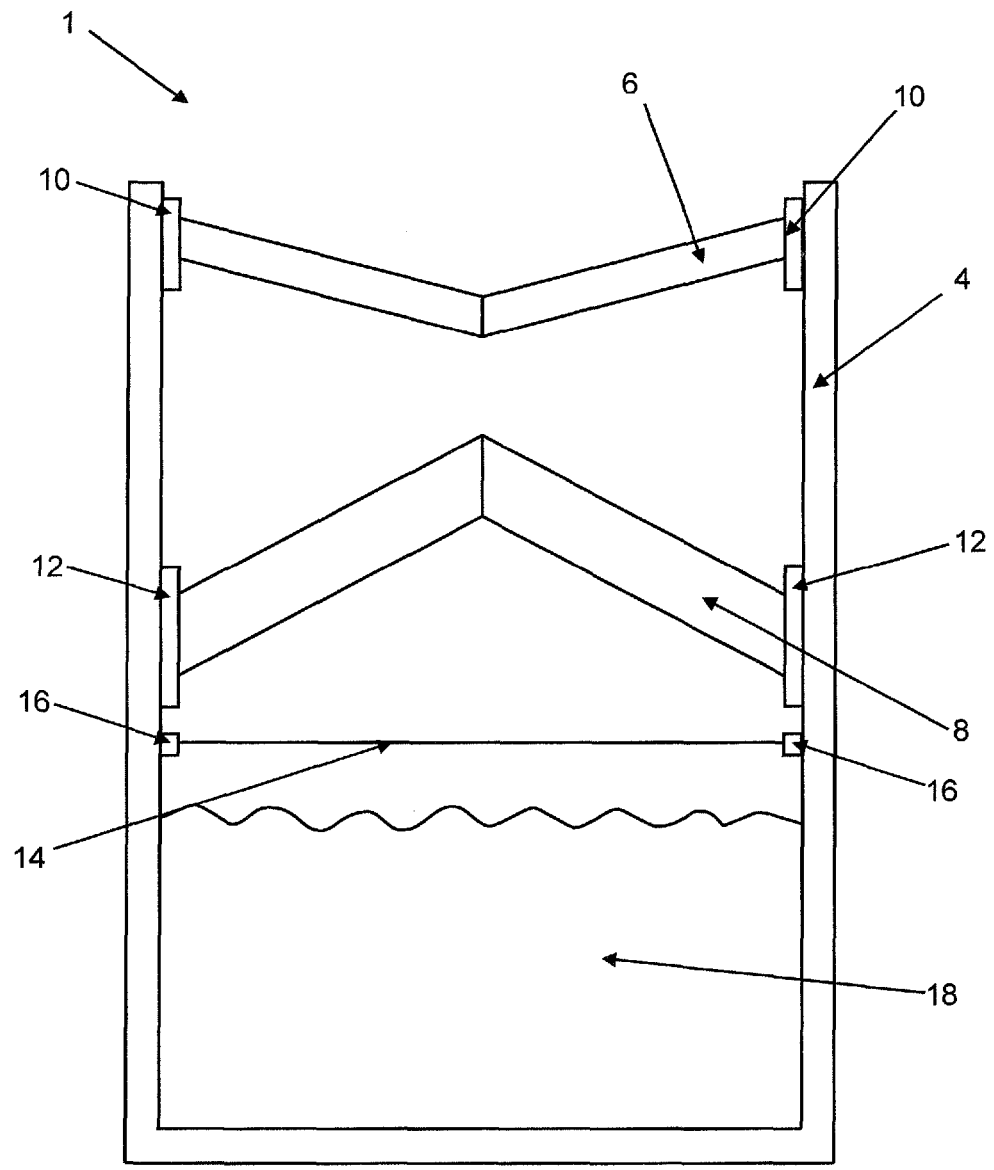
FIG. 1 is a schematic cross-sectional view of a device according to a preferred embodiment of the present invention.

Certain terminology is used in the following description for convenience only and is not limiting. The words "bottom" and "top" designate directions in the drawings to which reference is made. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals indicate like elements throughout the several views, FIG. 1 shows a schematic cross-sectional view of a device 1 according to a preferred embodiment of the present invention. The device 1 includes a container 4 preferably in the form of a jar that is open on its top. Side walls of the container 4 are preferably cylindrical and of even thickness. A wiper 6 is preferably arranged on the inside of the container 4 in the region of the opening, shortly below the opening, and closes the opening.

The floor and side walls of the container 4 and the wiper 6 are manufactured from a hydrophobic material or coated with a hydrophobic layer. Originating from the centre of the wiper 6, the wiper 6 is slitted or notched in eight directions.

The eight slits/notches (not shown) preferably do not reach all the way to the side walls of the container 4 and are meant to enable the introduction of a medical implant through the wiper 6. The wiper 6, thus, has eight flexible segments that wipe off the medical implant upon introducing and taking it out or upon pulling it out, meaning that they sweep over the surface of the implant. This ensures that the wiper 6 sweeps over essentially the entire surface of the medical implant, in particular when it is being pulled out, and thus wipes it off.

A transfer means 8, in which slits are arranged as well, is arranged inside the container 4. The transfer means 8 is manufactured from a flexible porous material, such as a sponge. The transfer means 8 is saturated with an aqueous solution comprising an antibiotic. The material is hydrophilic. This ensures that it can be soaked with an aqueous liquid. Owing to the hydrophobic properties of the container 4 and wiper 6, the aqueous liquid is situated in the transfer means 8.

The wiper 6 is supported through a bracketing ring 10 that is arranged in the region of the opening on the inside of the container 4. Likewise, the transfer means 8 is supported through a second bracketing ring 12. A reservoir groove capable of taking up excess of aqueous liquid can be provided in the second bracketing ring 12. This prevents the liquid contained in the transfer means 8 from flowing into the regions below the transfer means 8 in the container 4 when a pressure is applied to the transfer means 8, for example, when the transfer means 8 is being squeezed out. Part of the liquid retained in the bracketing ring 12 can then be soaked up again by the relaxing transfer means 8 and thus become available for a second application.

A membrane 14 is arranged below the transfer means 8 in the container 4 and is bracketed through a third bracketing ring 16 such as to be parallel to the floor of the container 4. The membrane 14 closes the container 4 in a sealed manner such that no contamination from outside and no droplets of the liquid contained in the transfer means 8 can penetrate into the region below the membrane 14. A powder 18 comprising a pharmaceutically active substance or a bone growth-promoting substance is contained below the membrane 14 in the container 4. The bone growth-promoting substance can, for example, be a mixture of calcium sulfate hemihydrate, calcium sulfate dihydrate, and ammonium sulfate, or it can be calcium phosphate. In this context, the grain size of the powder 18 can be less than 80 μm in order to coat the implants to be coated effectively and to ensure the usability of the pharmaceutically active or bone growth-promoting substances in the living body.

The device 1 shown can be used to carry out a method according to a preferred embodiment of the present invention. The transfer means 8 is soaked with an aqueous solution that contains at least one pharmaceutically effective substance to be used to coat a medical implant. The transfer means 8 can be soaked with the liquid through a connection (not shown). Alternatively, the transfer means 8 can be filled using a syringe proceeding through the wiper 6.

A medical implant (not shown) is pushed through the wiper 6 to meet the transfer means 8. Owing to the pressure exerted on the transfer means 8 through the medical implant, the medical implant not only pushes through the breaches designed for this purpose in the transfer means 8, but also the liquid contained in the pores of the transfer means 8 is pushed out of the transfer means 8 and applied to the surface of the medical implant.

Subsequently, the medical implant coated with the liquid punctures the membrane 16 which, until then, protected the powder 18 situated below it from external influences. The medical implant is then immersed in the powder 18. The liquid film on the surface of the medical implant causes the powder 18 to adhere well to the surface thereof.

Once the surface of the medical implant has been coated with the powder 18, the medical implant is pulled out of the container 4. The coated surface of the medical implant is pulled past the transfer means 8 and the wiper 6 in the process. Excess powder 18 and excess liquid is thus wiped off the surface of the medical implant. The medical implant pulled out of the container 4 is then coated, but does not drip any longer and does not release dust. Moreover, the inclination of the transfer means 8, which is provided as an envelope of cone and whose tip points in the direction of the wiper 6, prevents the liquid from splashing. These measures prevent the liquid and the powder 18 from contaminating the surroundings. The medical implant coated with the powder 18 and the liquid is then ready for use in a surgery.

The coating device 1 is manufactured from polypropylene, has a height of 25 cm and a diameter of 6 cm. The wiper 6 also consists of polypropylene. The transfer means 8 is a disc-shaped elastomer sponge (polyurethane sponge) and the membrane 14 is made of aluminum compound foil. The bracketing rings 10, 12, 16 of the wiper 6, transfer means 8, and membrane 14, respectively, are manufactured from polypropylene. The polypropylene rings 10, 12, 16 are pressed into the internal space of the container 4 in a press-fit. Before its use, the container 4 is closed in a germ-tight manner through an aluminum compound foil (not shown) that closes the opening of the container 4.

Figure 2:
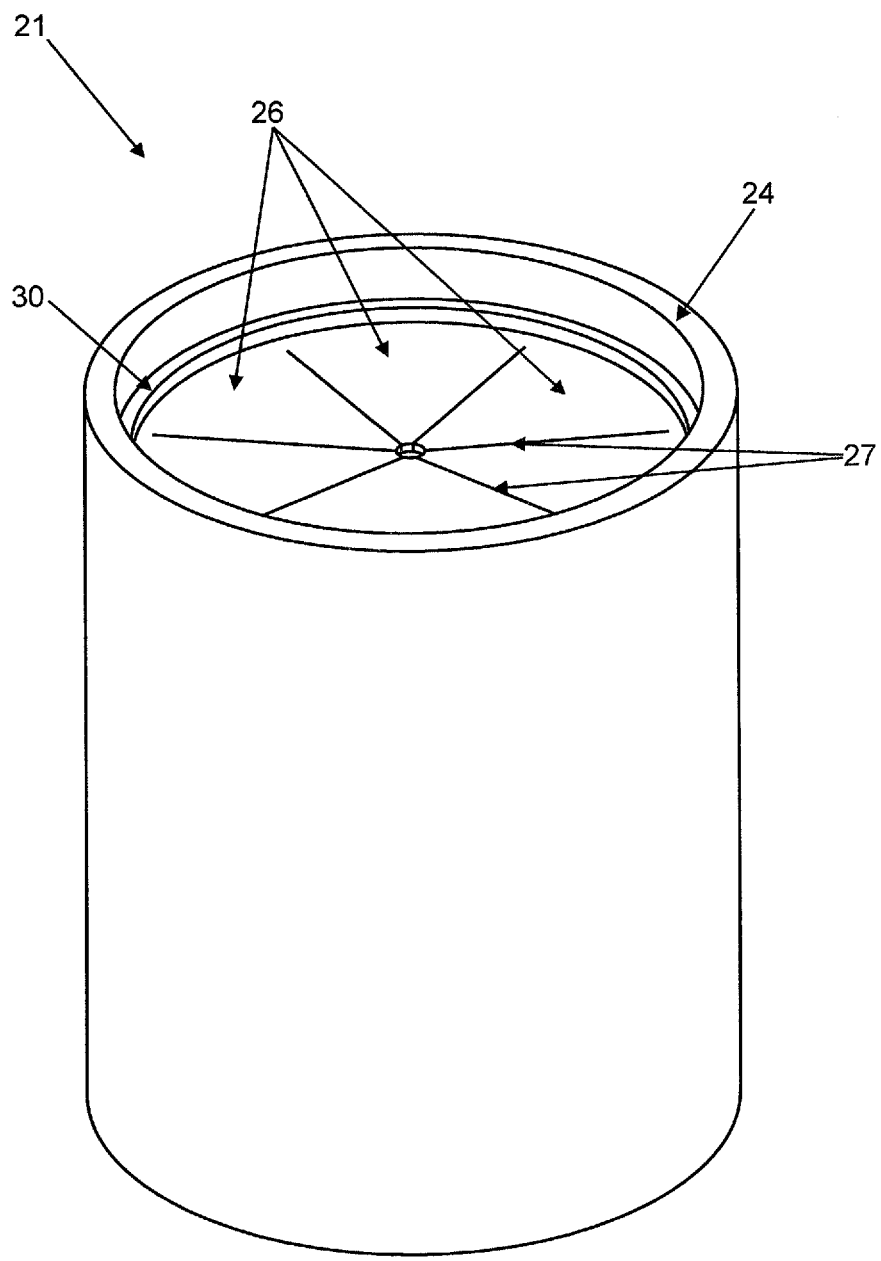
FIG. 2 is a schematic perspective view of a device according to a preferred embodiment of the present invention.

FIG. 2 shows a schematic perspective view of a second device 21 according to a preferred embodiment of the present invention for a method according to a preferred embodiment of the present invention. The device 21 includes a container 24 and a wiper 26 that preferably closes the container 24 on its top nearly completely except for a circular opening in the middle. The flexible wiper 26 has six slits 27 or notches 27 that connect the top of the wiper 26 to the bottom of the wiper 26 facing the inside of the container 24 such that a medical implant (not shown) can be introduced into the inside of the container 24 through the wiper 26 along the slits 27 which are folded down in this situation.

On the inside of the container 24 is situated a powder (not shown), into which a medical implant being inserted into the container 24 can be immersed or onto which the medical implant can be pressed. In order to prevent contamination of the powder in the container 24, the powder can be covered through a membrane (not shown) that is arranged on the inside of the container 24 and gets punctured by the medical implant. The wiper 26 ensures that any excess of powder is wiped off the surface of the medical implant when the implant is pulled out of the container 24.

According to a preferred embodiment of the present invention, common Zweymüller hip endoprostheses can be briefly inserted to the end of the stem into the devices 1, 21 filled with powder and liquid or just with powder, and can then be pulled out again instantaneously. The Zweymüller hip endoprostheses are thus furnished with a powder coating and, if applicable, also a liquid film at the stem surface. If both a powder and a liquid are used, the Zweymüller hip endoprostheses have a white coating at the stem surface which hardens within maximally 30 seconds and adheres to the surface. The hip endoprostheses are thus ready for use in a surgery.

Examples of the production of powders and liquids for a method according to a preferred embodiment of the present invention and another example of a device according to a preferred embodiment of the present invention are illustrated in the following.

EXAMPLE 1

Device According to the Invention

A container that is closed by a membrane is filled with a powder mixture of 150 g calcium sulfate hemihydrate (sieve fraction <64 μm), 15.0 g calcium sulfate dihydrate (sieve fraction <64 μm), and 1.5 g ammonium sulfate (sieve fraction <64 μm).

EXAMPLE 2

Device According to the Invention

The container from example 1 is filled with a powder mixture of 100 g calcium sulfate hemihydrate (sieve fraction <64 μm), 50.0 g calcium carbonate (sieve fraction <64 μm), 15.0 g calcium sulfate dihydrate (sieve fraction <64 μm), and 1.5 g ammonium sulfate.

EXAMPLE 3

Device According to the Invention

The container from example 1 is filled with 150 g β-tricalcium phosphate (sieve fraction <64 μm).

EXAMPLE 4

Device According to the Invention

The container from example 1 is filled with 150 g α-tricalcium phosphate (sieve fraction <64 μm).

EXAMPLE 5

Device According to the Invention

The container from example 1 is filled with 150 g α-tetracalcium phosphate (sieve fraction <64 μm).

EXAMPLE 6

Production of a Coating Solution Containing Gentamicin Sulfate

A total of 16.0 g gentamicin sulfate (Fujian Fukang Ltd.) were mixed with 4.0 ml pyrogen-free sterile water at room temperature. After stirring with a magnetic stirrer for 24 hours at room temperature, an oily-viscous yellowish solution had formed. A coating solution containing gentamicin sulfate as liquid for coating a medical implant was thus obtained.

EXAMPLE 7

Production of a Coating Solution Containing the Two-Component Combination of Gentamicin Sulfate and Clindamycin Hydrochloride A total of 12.0 g gentamicin sulfate (Fujian Fukang Ltd.) were mixed with 4.0 g clindamycin hydrochloride (Sigma-Aldrich), and 4.0 ml pyrogen-free sterile water at room temperature. After stirring with a magnetic stirrer for 24 hours at room temperature, an oily-viscous yellowish solution had formed.

EXAMPLE 8

Production of a Coating Solution Containing the Three-Component Combination of Gentamicin Sulfate, Clindamycin Hydrochloride, and Vancomycin Hydrochloride A total of 4.0 g gentamicin sulfate (Fujian Fukang Ltd.), 4.0 g clindamycin hydrochloride (Sigma-Aldrich), and 4.0 g vancomycin hydrochloride (Sigma-Aldrich) were mixed with 8.0 ml pyrogen-free sterile water at room temperature. After stirring with a magnetic stirrer for 24 hours at room temperature, a viscous yellowish solution had formed.

EXAMPLE 9

Production of a Coating Solution Containing Gentamicin Sulfate and Malic Acid

A total of 100 mg malic acid and 16.0 g gentamicin sulfate (Fujian Fukang Ltd.) were mixed with 4.0 ml pyrogen-free sterile water at room temperature. After stirring with a magnetic stirrer for 24 hours at room temperature, an oily-viscous yellowish solution had formed.

EXAMPLE 10

Production of a Coating Solution Containing Gentamicin Sulfate and Citric Acid

A total of 100 mg citric acid and 16.0 g gentamicin sulfate (Fujian Fukang Ltd.) were mixed with 4.0 ml pyrogen-free sterile water at room temperature. After stirring with a magnetic stirrer for 24 hours at room temperature, an oily-viscous yellowish solution had formed.

Examples 11-15

Production of a Device According to the Invention Comprising a Powder Containing a Bone Growth Promoting Substance and a Transfer Means Containing a Pharmaceutically Effective Substance The container from example 1 was initially provided with a transfer means that can be deformed elastically. Then, conventional 10 ml plastic syringes were used to draw up 5 ml each of the coating solutions of examples 6-10 and the filled plastic syringes were used to squirt 4 ml of the corresponding agent solution onto the porous transfer means of the device. The agent solution was thus soaked up through the porous transfer means.

The features of the present invention disclosed in the preceding description and in the claims, figures, and exemplary embodiments, can be essential for the implementation of the various embodiments of the invention both alone and in any combination.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for coating at least regions of a medical implant, the method comprising:
   providing powder in a container having an opening, the powder comprising at least one pharmaceutically active substance or one bone growth-promoting substance, the container having a membrane that seals the powder in the container;
   introducing a least a portion of a medical implant through the opening in the container, wherein the medical implant is pushed through the membrane or the membrane is opened;
   contacting a surface of the medical implant with the powder after the introducing;

transferring powder to the surface of the medical implant through the contacting such that at least some of the powder adheres to the surface of the medical implant after the contacting;

pulling the medical implant out of the container after powder is transferred to the surface of the medical implant;

immersing the surface of the medical implant into a liquid, painting the surface of the medical implant, or wetting the surface of the medical implant with a liquid prior to contacting the surface of the medical implant with powder;

sweeping the medical implant over an elastically deformable transfer means; and transferring the liquid from the transfer means to the surface of the medical implant while the medical implant is swept over the transfer means.

2. The method according to claim 1, wherein at least 90% of the medical implant is coated.

3. The method according to claim 1, further comprising:
whirling up the powder through a flow of air in order to attain complete coating of the medical implant.

4. A method for coating at least regions of a medical implant, the method comprising:

providing powder in a container having an opening, the powder comprising at least one pharmaceutically active substance or one bone growth-promoting substance;

introducing a least a portion of a medical implant through the opening in the container;

contacting a surface of the medical implant with the powder;

transferring power to the surface of the medical implant through the contacting such that at least some of the powder adheres to the surface of the medical implant after the contacting;

whirling up the powder through a flow of air in order to attain complete coating of the medical implant;

pulling the medical implant out of the container after powder is transferred to the surface of the medical implant;

immersing the surface of the medical implant into a liquid, painting the surface of the medical implant, or wetting the surface of the medical implant with a liquid prior to contacting the surface of the medical implant with powder;

sweeping the medical implant over an elastically deformable transfer means; and transferring the liquid from the transfer means to the surface of the medical implant while the medical implant is swept over the transfer means.

\* \* \* \* \*